United States Patent
Jin et al.

(10) Patent No.: US 9,861,339 B2
(45) Date of Patent: Jan. 9, 2018

(54) ULTRASONIC DIAGNOSTIC APPARATUS

(71) Applicant: SAMSUNG MEDISON CO., LTD., Gangwon-Do (KR)

(72) Inventors: Gil Ju Jin, Seoul (KR); Kyeong Gu Woo, Suwon-si (KR); Sim Gwan Jeong, Gyeongsangnam-do (KR); Hae Ran Choi, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 16 days.

(21) Appl. No.: 14/455,400

(22) Filed: Aug. 8, 2014

(65) Prior Publication Data
US 2015/0045672 A1 Feb. 12, 2015

(30) Foreign Application Priority Data
Aug. 9, 2013 (KR) .................. 10-2013-0094515

(51) Int. Cl.
*A61B 8/00* (2006.01)
*G01S 7/52* (2006.01)
(Continued)

(52) U.S. Cl.
CPC ............ *A61B 8/4405* (2013.01); *A61B 8/462* (2013.01); *A61B 8/467* (2013.01); *F16M 11/043* (2013.01);
(Continued)

(58) Field of Classification Search
CPC ..... A61B 8/4405; A61B 8/4444; A61B 8/462; A61B 8/467
See application file for complete search history.

(56) References Cited

U.S. PATENT DOCUMENTS

| 2004/0068185 A1* | 4/2004 | Marshall .............. A61B 8/4405 600/437 |
| 2010/0094130 A1* | 4/2010 | Ninomiya ................ A61B 8/00 600/437 |

(Continued)

FOREIGN PATENT DOCUMENTS

| EP | 2 092 892 A1 | 8/2009 |
| WO | 2005/074807 A1 | 8/2005 |

OTHER PUBLICATIONS

European Search Report issued in corresponding European Patent Application No. 14172456.6 dated Feb. 5, 2015.
(Continued)

*Primary Examiner* — Baisakhi Roy
(74) *Attorney, Agent, or Firm* — McDermott Will & Emery LLP (57) ABSTRACT

Disclosed is an ultrasonic diagnostic apparatus including a main body, at least one input/output unit coupled to one side of the main body to input data to the main body or to output data transmitted from the main body, and a connection unit to connect the input/output unit and the main body to each other. The connection unit includes plural first connection members, each of which is connected at one end thereof to the main body and at the other end thereof to at least a portion of the input/output unit and has a variable length to move the input/output unit relative to the main body, and at least one second connection member coupled to the first connection members and at least one of the main body or the input/output unit so as to come into contact with the same at a point to support load of the input/output unit.

19 Claims, 11 Drawing Sheets

(51) Int. Cl.
*F16M 11/04* (2006.01)
*F16M 11/12* (2006.01)
*F16M 11/42* (2006.01)

(52) U.S. Cl.
CPC ........... *F16M 11/121* (2013.01); *F16M 11/42* (2013.01); *G01S 7/52084* (2013.01)

(56) References Cited

U.S. PATENT DOCUMENTS

| | | | | |
|---|---|---|---|---|
| 2012/0182709 | A1* | 7/2012 | Asai | A61B 8/462 |
| | | | | 361/810 |
| 2014/0117635 | A1* | 5/2014 | Ninomiya | A61B 8/4405 |
| | | | | 280/35 |
| 2015/0045672 | A1* | 2/2015 | Jin | G01S 7/52084 |
| | | | | 600/459 |
| 2015/0094578 | A1* | 4/2015 | Ninomiya | A61B 8/4411 |
| | | | | 600/437 |

OTHER PUBLICATIONS

European Communication pursuant to Article 94(3) EPC, issued in corresponding European Patent Application No. 14 173 456.6, dated Feb. 9, 2017.

* cited by examiner

ULTRASONIC DIAGNOSTIC APPARATUS

CROSS-REFERENCE TO RELATED APPLICATION

This application claims the benefit of Korean Patent Application No. 2013-0094515, filed on Aug. 9, 2013 in the Korean Intellectual Property Office, the disclosure of which is incorporated herein by reference.

BACKGROUND

1. Field

Embodiments of the present invention relate to an ultrasonic diagnostic apparatus having an improved configuration of a connection unit to change a position of an input/output unit.

2. Description of the Related Art

Generally, an ultrasonic diagnostic apparatus is designed to emit ultrasonic waves from the surface of the body of an object toward a region in the body to be diagnosed and to acquire tomograms of soft tissues or images of blood stream.

A typical ultrasonic diagnostic apparatus includes a main body, a probe configured to transmit ultrasonic signals to an object and to receive signals reflected from the object, a display unit disposed above the main body to display images of diagnostic results based on the received ultrasonic signals, and a control panel disposed in front of the display unit to allow a user to operate the ultrasonic diagnostic apparatus.

In the above described ultrasonic diagnostic apparatus, the control panel and the display unit are adjustable in height and position based on shape of the user and use environment.

Conventionally, since vertical movement and rotation of an input/output unit such as the control panel and the display unit have been realized respectively via separate mechanisms therefor, a great number of elements may be necessary, causing problems upon production.

SUMMARY

It is an aspect of the present invention to provide an ultrasonic diagnostic apparatus having an improved configuration of a connection unit to enable simultaneous implementation of vertical movement, horizontal movement, and rotation of an input/output unit.

Additional aspects of the invention will be set forth in part in the description which follows and, in part, will be obvious from the description, or may be learned by practice of the invention.

In accordance with one aspect of the invention, an ultrasonic diagnostic apparatus includes a main body, at least one input/output unit coupled to one side of the main body to input data to the main body or to output data transmitted from the main body, and a connection unit to connect the input/output unit and the main body to each other, wherein the connection unit includes a plurality of first connection members, each of which is connected at one end thereof to the main body and at the other end thereof to at least a portion of the input/output unit and has a variable length to move the input/output unit relative to the main body, and at least one second connection member coupled to the first connection members and at least one of the main body or the input/output unit so as to come into contact with the same at a point to support load of the input/output unit.

Each of the first connection members may include a first main body coupling part coupled to the main body and a first input/output unit coupling part coupled to the input/output unit, the second connection member may include a second main body coupling part coupled to the main body and a second input/output unit coupling part coupled to the input/output unit, the first main body coupling part and the second main body coupling part may be arranged in a first plane, and the first input/output coupling part and the second input/output coupling part may be arranged in a second plane.

The first plane and the second plane may be different planes.

Two first connection members and one second connection member may be arranged to provide the connection unit with a triangular pyramid shape.

Two first connection members and two second connection members may be arranged to provide the connection unit with a quadrangular pyramid shape.

The first plane may be at least one of a circular plane or an oval plane.

The first main body coupling part, the first input/output unit coupling part, the second main body coupling part, and the second input/output coupling part may be at least one of ball joints and universal joints.

The connection unit may be manually movable.

The connection unit may be automatically movable.

The at least one input unit may include a control panel to input a signal to the main body.

The at least one input unit may include a display to output a signal generated in the main body.

In accordance with another aspect of the invention, an ultrasonic diagnostic apparatus includes a main body, at least one input/output unit coupled to one side of the main body to input data to the main body or to output data transmitted from the main body, and a connection unit to connect the input/output unit and the main body to each other, the length of at least a portion of the connection unit being variable to allow the connection unit to move relative to the main body, wherein the connection unit is coupled at a plurality of points to at least one of the main body and the input unit to enable load distribution.

The connection unit may include a plurality of first connection members having a variable length, and at least one second connection member coupled to the first connection members and at least one of the main body or the input/output unit so as to come into contact with the same at a point.

Each of the first connection members may include a first main body coupling part coupled to the main body and a first input/output unit coupling part coupled to the input/output unit, the second connection member may include a second main body coupling part coupled to the main body and a second input/output unit coupling part coupled to the input/output unit, and the first input/output coupling part and the second input/output coupling part may come into contact with each other at a point.

The first main body coupling part and the second main body coupling part may be arranged in a first plane, and the first input/output coupling part and the second input/output coupling part may be arranged in a second plane, and the first plane and the second plane may be different planes.

Two first connection members and one second connection member may be arranged to provide the connection unit with a triangular pyramid shape.

Two first connection members and two second connection members may be arranged to provide the connection unit with a quadrangular pyramid shape.

The first plane may be at least one of a circular plane or an oval plane.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Reference will now be made in detail to the embodiments of the present invention, examples of which are illustrated in the accompanying drawings, wherein like reference numerals refer to like elements throughout.

Figure 1:
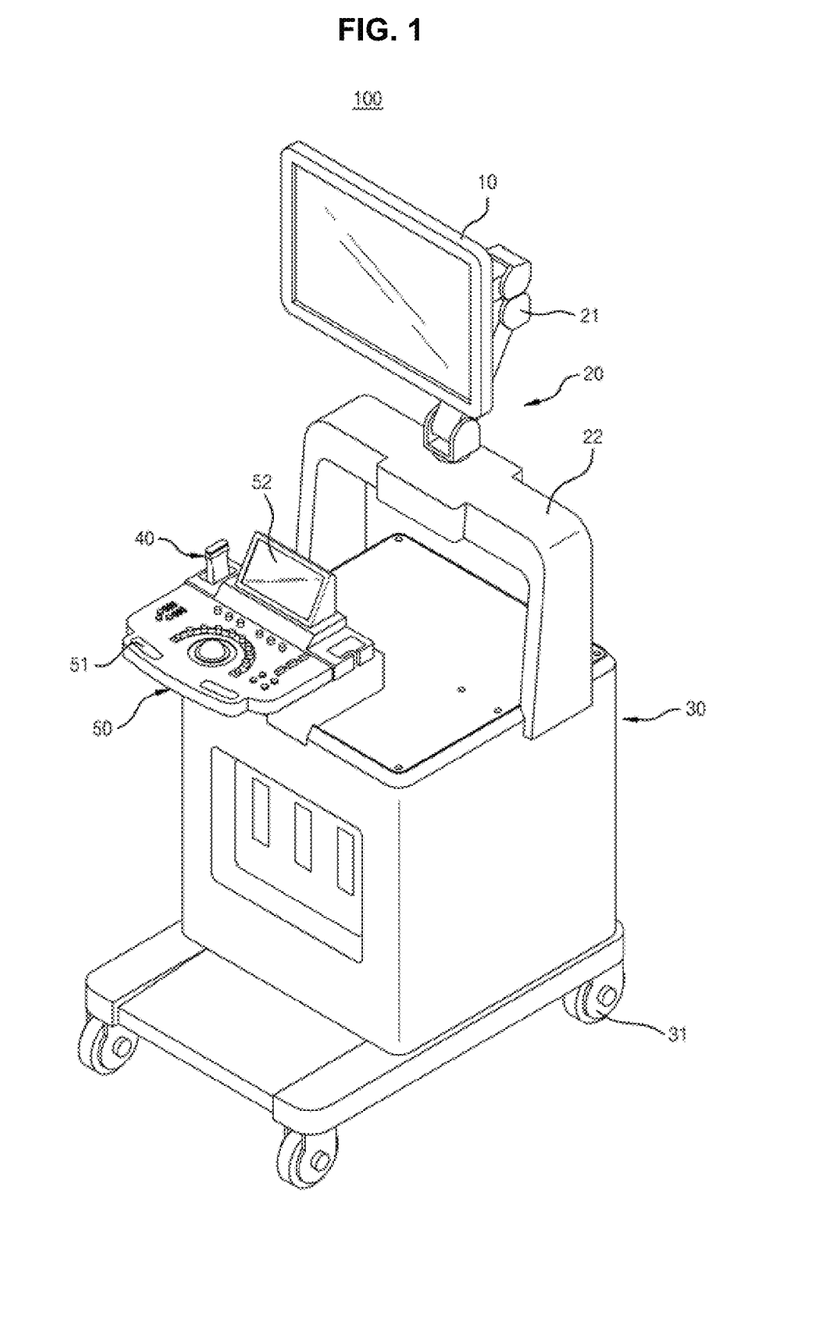
FIG. 1 is a view showing an ultrasonic diagnostic apparatus in accordance with one embodiment of the present invention.

FIG. 1 is a view showing an ultrasonic diagnostic apparatus in accordance with one embodiment of the present invention.

As exemplarily shown in FIG. 1, the ultrasonic diagnostic apparatus 100 includes a main body 30, a probe 40 configured to transmit ultrasonic signals to an object to be diagnosed and to receive the signals reflected from the object, a main display 10 disposed above the main body 30 to display images of diagnostic results based on the received ultrasonic signals, and a control panel 50 to allow a user to operate the ultrasonic diagnostic apparatus 100. An auxiliary display 52 may be provided on one side of the control panel 50.

Wheels 31 for movement of the ultrasonic diagnostic apparatus 100 may be mounted at the bottom of the main body 30. The control panel 50 and the display 10 are horizontally movable by movement of the main body 30.

A grip portion 51 may protrude forward from the control panel 50. The user may grip the grip portion 51 to horizontally move the ultrasonic diagnostic apparatus 100 including the control panel 50. In addition, the user may move the control panel 50 vertically or horizontally by applying force to the grip portion 51 in a given direction. The grip portion 51 may be provided with a switch (not shown), and in this case, the user may automatically control movement of the ultrasonic diagnostic apparatus 100.

The control panel 50 serves as an input unit to input data to the main body 30. The display 10 serves as an output unit to output data transmitted from the main body 30. In one embodiment of the present invention, the auxiliary display 52 provided on the control panel 50 also serves as the output unit. The control panel 50, the display 10, and the auxiliary display 52 are referred to as an input/output unit 70.

Although the control panel 50 will hereinafter be described by way of example, the following description is not limited thereto and the embodiment of the present invention may be applied to other elements coupled to the main body 30 of the ultrasonic diagnostic apparatus 100.

The ultrasonic diagnostic apparatus 100 may further include a connection unit 60 to adjust a position of the input/output unit 70, more particularly, the control panel 50 and the display 10, based on shape of the user or use environment of the ultrasonic diagnostic apparatus 100. This will be described below.

In one embodiment, a connection unit 20 may be located between the display 10 and the main body 30 to couple the display 10 and the main body 30 to each other. The connection unit 20 may include a connection member 21 coupled to the display 10 and a support member 22 coupled to the main body 30. Through provision of the support member 22, a space is defined between the display 10 and the main body 30, which enables reception of elements required for ultrasonic diagnosis.

Figure 2:
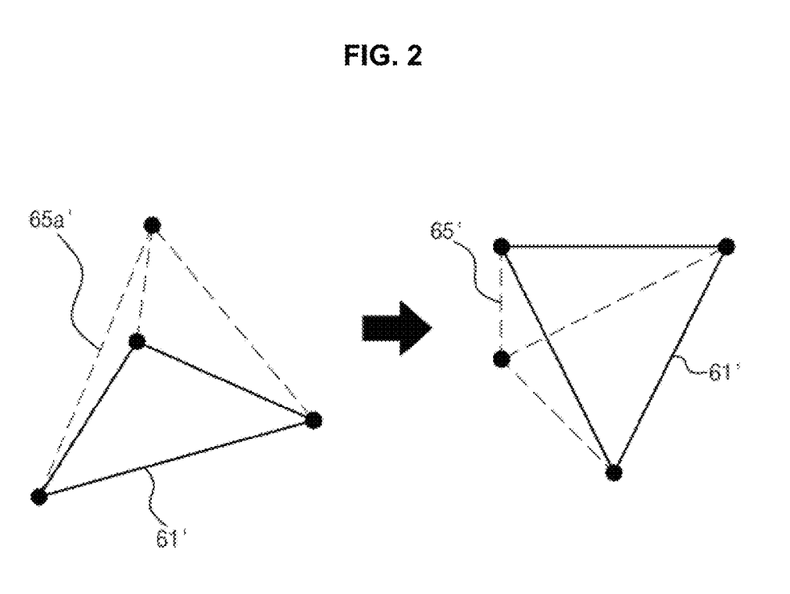
FIG. 2 is a view schematically showing the structure of a connection unit in accordance with one embodiment of the present invention.
Figure 3:
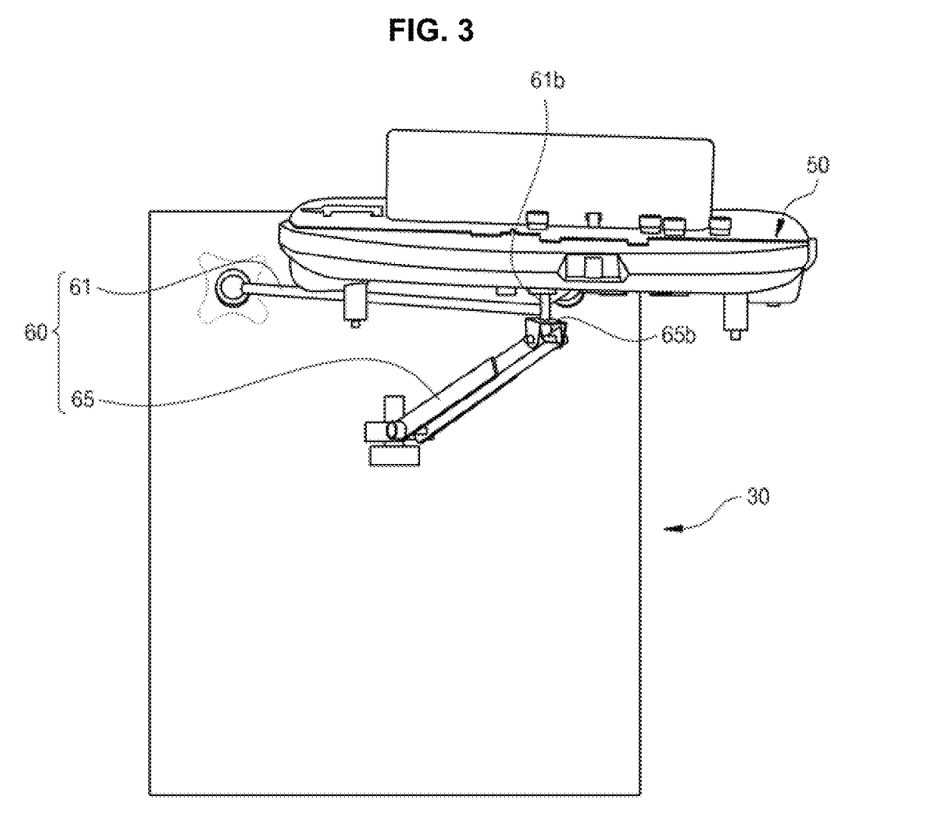
FIG. 3 is a view showing a coupled state of a control panel and a main body in accordance with one embodiment of the present invention.
Figure 4:
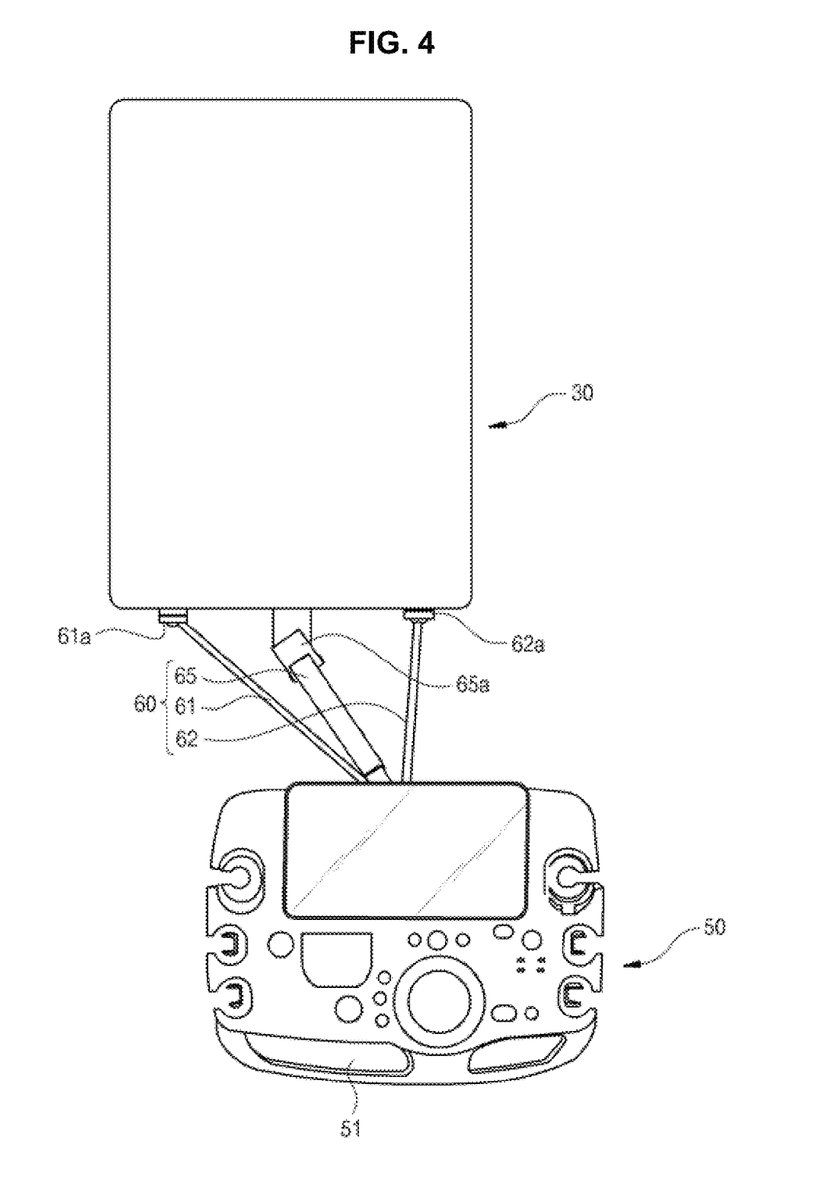
FIG. 4 is a view showing the coupled state of the control panel and the main body in accordance with one embodiment of the present invention when viewed at a different angle from FIG. 3.

FIG. 2 is a view schematically showing the structure of the connection unit in accordance with one embodiment of the present invention, FIG. 3 is a view showing a coupled state of the control panel and the main body in accordance with one embodiment of the present invention, and FIG. 4 is a view showing the coupled state of the control panel and the main body in accordance with one embodiment of the present invention when viewed at a different angle from FIG. 3.

As exemplarily shown in FIGS. 2 to 4, the main body 30 and the control panel 50 are coupled to each other via the connection unit 60. The connection unit 60 includes a plurality of connection members 61, 62, 65. Each of the connection members 61, 62, 65 is connected at one end thereof to the main body 30 and at the other end thereof to at least a portion of the input/output unit, more particularly, the control panel 50, to move the control panel 50 relative to the main body 30. A variable length connection member is referred to as a first connection member 65, and a load support connection member is referred to as a second connection member 61; 62. In one embodiment of the present invention, the second connection member 61; 62 may also have a variable length.

A plurality of second connection members 61, 62 may be provided, and at least one first connection member 65 may be provided. As exemplarily shown in the drawings, two second connection members 61, 62 and one first connection member 65 may be provided, although the disclosure is not limited thereto.

The second connection members 61, 62 and the first connection member 65 may be coupled to come into contact with one another at a point. As exemplarily shown in the drawings, the control panel 50 is mounted at a point where the second connection members 61, 62 and the first connection member 65 come into contact with one another. The second connection members 61, 62 may include second main body coupling parts 61a, 62a coupled to the main body 30, and second input/output unit coupling parts 61b, 62b coupled to the input/output unit. The first connection member 65 may include a first main body coupling part 65a coupled to the main body 30, and a first input/output unit coupling part 65b coupled to the input/output unit. That is, the second input/output unit coupling parts 61b, 62b and the first input/output unit coupling part 65b may come into contact with one another at a point.

The second main body coupling parts 61a, 62a, the second input/output coupling parts 61b, 62b, the first main body coupling part 65a, and the first input/output unit coupling part 65b, which are coupled to the main body 30 or the input/output unit 50; 10, may be at least one of ball joints or universal joints.

A plane in which the second main body coupling parts 61a, 62a and the first main body coupling part 65a are located on the main body 30 is referred to as a first plane, and a plane in which the second input/output unit coupling parts 61b, 62b and the first input/output coupling part 65b are located on the control panel 50 is referred to as a second plane. The first plane and the second plane are different planes, and thus the connection unit 60 may have a 3-dimensional arrangement in a plurality of planes.

In one embodiment of the present invention, two second connection members 61, 62 and one first connection member 65 may be provided such that a total of three connection members 61, 62, 65 extend from one point of the control panel 50 to thereby be coupled to the main body 30. As such, the connection unit 60 achieves a triangular pyramidal structure of coupling the main body 30 and the control panel 50 to each other. Movement of the control panel 50 will be described below.

The ultrasonic diagnostic apparatus 100 includes the input/output unit 70 to input data to the main body 30 or to output data transmitted from the main body 30, and the connection unit 60 to couple the input/output unit 70 and the main body 30 to each other. In addition, a controller (not shown) may be provided to control movement of the connection unit 60 in response to user operation detected by the input/output unit 70. The controller (not shown) may be mounted in the main body 30.

The connection unit 60 may be manually moved by force applied to the input/output unit 70 by the user. In this case, the input/output unit 70 may detect variation of pressure applied by the user or variation of a user contact position and transmit the detected result to the controller (not shown).

Of course, the disclosure is not limited to the above description, and the connection unit 60 may be automatically moved via user operation. In this case, the connection unit 60 may initiate or stop movement in response to a control signal of the controller (not shown).

Movement of the control panel 50 will hereinafter be described with reference to FIGS. 5 to 8. In the embodiment as exemplarily shown in FIGS. 5 to 8, both the first connection member 65 and the second connection members 61, 62 are length variable.

Figure 5:
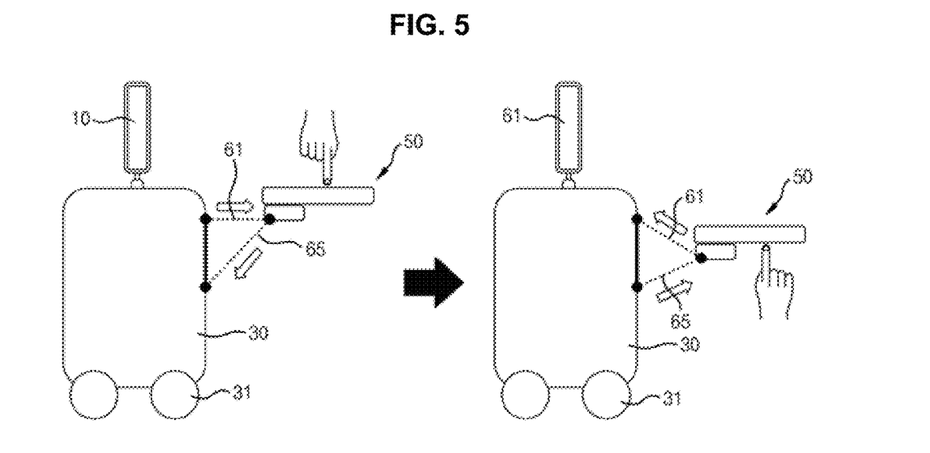
FIG. 5 is a view showing upward or downward movement of the control panel in accordance with another embodiment of the present invention.

FIG. 5 is a view showing upward or downward movement of the control panel in accordance with another embodiment of the present invention.

As exemplarily shown in FIG. 5, the user may move the control panel 50 upward or downward. When attempting to move the control panel 50 downward, the length of the second connection members 61, 62 is increased and the length of the first connection member 65 is reduced, causing downward movement of the control panel 50.

When attempting to move the control panel 50 upward, contrary to the above described downward movement, the length of the second connection members 61, 62 which have been increased is reduced and the length of the first connection member which has been reduced is increased, causing upward movement of the control panel 50.

Figure 6:
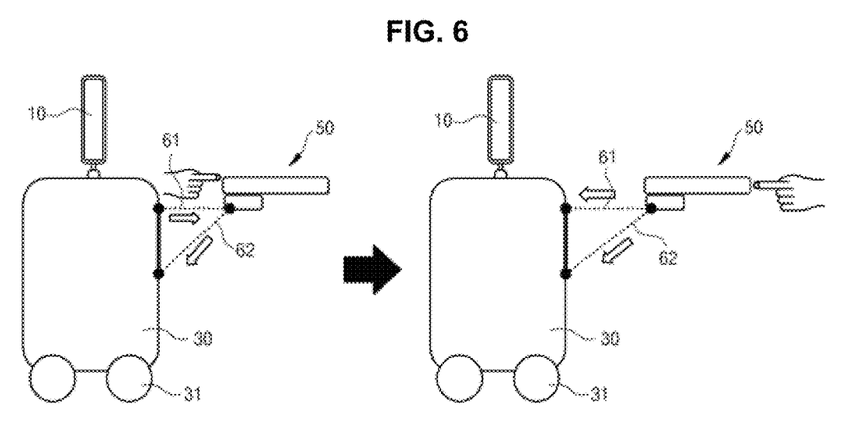
FIG. 6 is a view showing forward or rearward movement of the control panel in accordance with another embodiment of the present invention.

FIG. 6 is a view showing forward or rearward movement of the control panel in accordance with another embodiment of the present invention.

As exemplarily shown in FIG. 6, the user may move the control panel 50 forward or rearward. When attempting to move the control panel 50 forward, the length of the two second connection members 61, 62 is increased and the length of one first connection member 65 is increased, causing forward movement of the control panel 50.

When attempting to move the control panel 50 rearward, i.e. to move the forwardly moved control panel 50 toward the main body 30, the length of the two second connection members 61, 62 is reduced and the length of one first connection member is reduced, causing the control panel 50 to move toward the main body 30.

Figure 7:
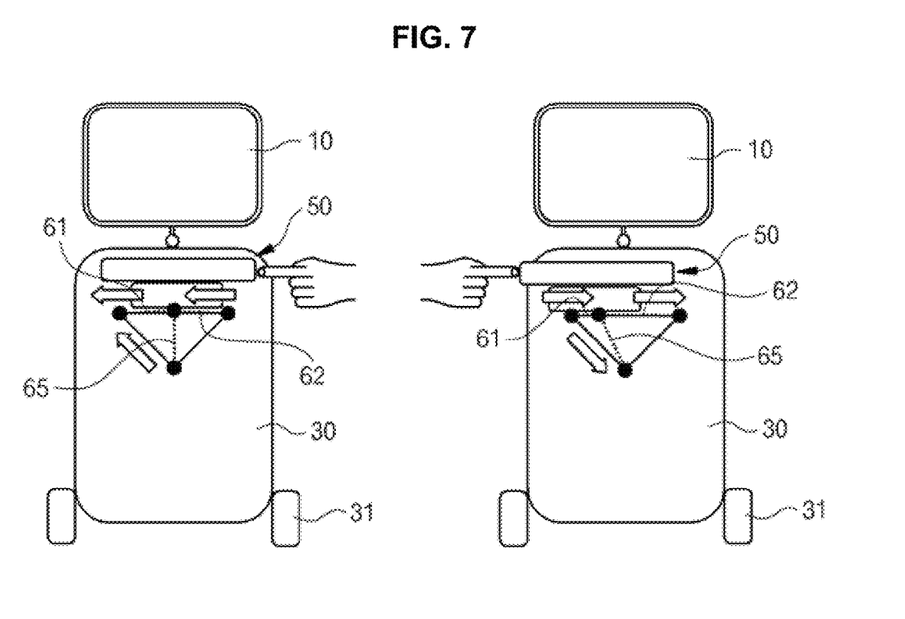
FIG. 7 is a view showing leftward or rightward movement of the control panel in accordance with another embodiment of the present invention.
Figure 8:
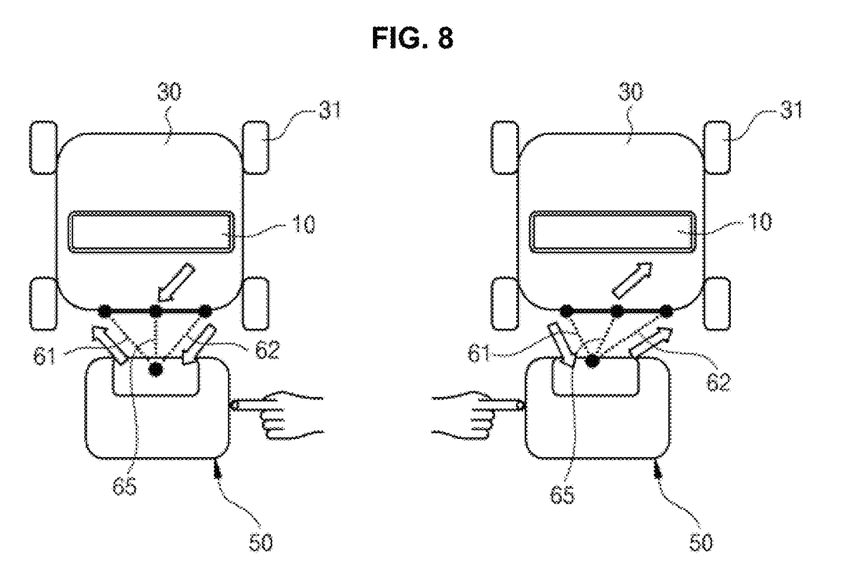
FIG. 8 is a view showing leftward or rightward movement of the control panel in accordance with another embodiment of the present invention when viewed at a different angle from FIG. 7.

FIG. 7 is a view showing leftward or rightward movement of the control panel in accordance with another embodiment of the present invention, and FIG. 8 is a view showing leftward or rightward movement of the control panel in accordance with another embodiment of the present invention when viewed at a different angle from FIG. 7.

As exemplarily shown in FIGS. 7 and 8, the user may move the control panel 50 leftward or rightward relative to the main body 30.

When attempting to move the control panel 50 leftward relative to the main body 30, the length of the left second connection member 61 among the two second connection members 61, 62 is reduced and the length of the right second connection member 62 is increased. The length of the first connection member 65 is also increased. Thereby, the first connection member 65 is moved leftward, causing leftward movement of the control panel 50.

When attempting to move the control panel 50 rightward relative to the main body 30, the length of the right second connection member 62 among the two second connection members 61, 62 is reduced and the length of the left second connection member 61 is increased. The length of the first connection member 65 is also increased. Thereby, the first connection member 65 is moved rightward, causing rightward movement of the control panel 50.

In one embodiment of the present invention, since the respective connection members 61, 62, 65 are arranged to share a plurality of planes to realize a 3-dimensional structure of the connection unit 60, more effective distribution of load applied to the respective connection members 61, 62, 65 may be accomplished than in conventional configurations. In this way, the single connection unit 60 may serve to support the input/output unit 70 having great load. In addition, effective fixing of the input/output unit 70 may be accomplished owing to excellent fastening strength.

Figure 9:
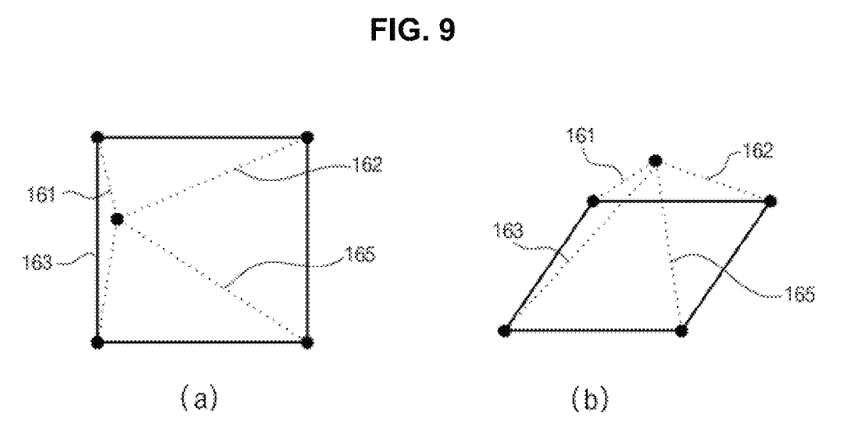
FIG. 9 is a view schematically showing the structure of a connection unit in accordance with another embodiment of the present invention.
Figure 10:
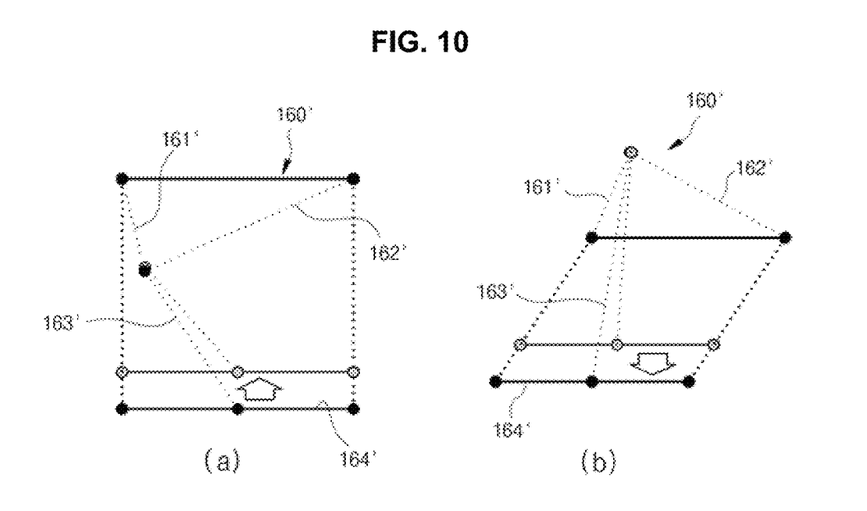
FIG. 10 is a view schematically showing the structure of a connection unit in accordance with another embodiment of the present invention.

FIGS. 9 and 10 are views schematically showing the structure of a connection unit in accordance with other embodiments of the present invention.

As exemplarily shown in FIG. 9, a connection unit 160 may have a quadrangular pyramid shape.

As exemplarily shown in the drawing, two first connection members 161, 162 and two second connection members 163, 165 may be provided, but the present embodiment is not limited thereto, and two first connection members and one second connection member may be provided.

As exemplarily shown in FIG. 10, a connection unit 160' may have a modified tetrahedral shape. In this case, the connection unit 160' may include a first connection member 163' and second connection members 161', 162'.

In one embodiment of the present invention as exemplarily shown in FIG. 10, the connection unit 160' may further include a vertically movable third connection member 164'. The length of the first connection member 163' is variable as the third connection member 164' is vertically moved, causing movement of an input/output unit (not shown) coupled to an apex.

The embodiments of the present invention as exemplarily shown in FIGS. 9 and 10 employ a greater number of connection members 161, 162, 163, 165; 161', 162', 163', 164' than those of the embodiments as exemplarily shown in FIGS. 1 to 8, thus achieving wider load distribution. This may realize more efficient support for an input/output unit having a great load.

Figure 11:
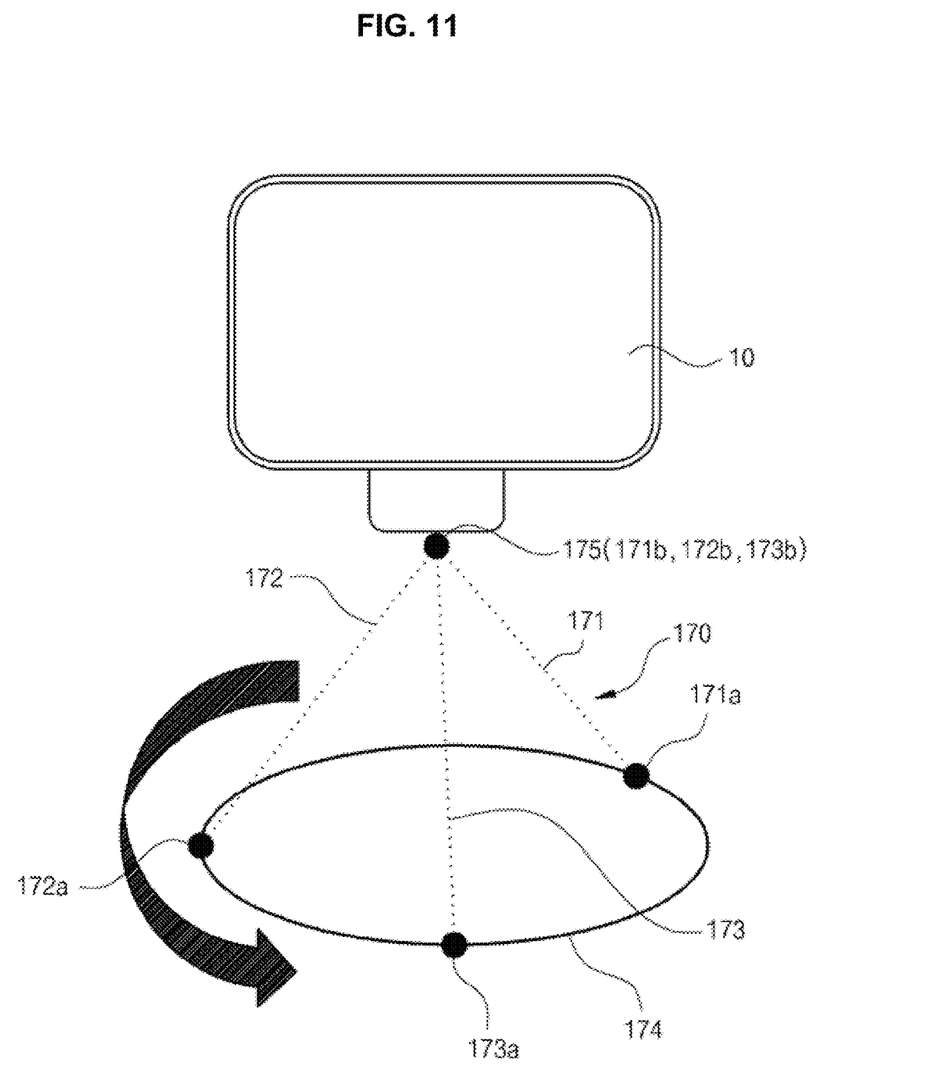
FIG. 11 is a view schematically showing the structure of a connection unit for a display in accordance with a further embodiment of the present invention.

FIG. 11 is a view schematically showing the structure of a connection unit for the display in accordance with a further embodiment of the present invention.

As exemplarily shown in FIG. 11, a connection unit 170 may be located between the display 10 and a main body (not shown). In one embodiment of the present invention, the connection unit 170 may have a conical shape. Three connection members 171, 172, 173 may be provided as exemplarily shown in the drawing, but the embodiment is not limited thereto.

The respective connection members may include an input/output unit coupling part 175 coupled to the display 10, and main body coupling parts 171a, 172a, 173a coupled to the main body (not shown). In the drawing, the input/output coupling part 175 corresponds to an apex of a cone.

In the case of the conical connection unit 170, a disc-shaped base 174 may be additionally coupled to the connection members 171, 172, 173. In this case, the input/output unit 70 including the display 10 may be rotated via rotation of the base 174. In addition, the display 10 may be vertically or horizontally moved via variation in the length of the connection members 171, 172, 173.

As is apparent from the above description, an ultrasonic diagnostic apparatus in accordance with the embodiment of the present invention provides a connection unit to simultaneously implement vertical movement and rotation. Further, the connection unit includes a plurality of connection members to support load of an input/output unit, which realizes load distribution and support of a greater load. Furthermore, a simplified coupling configuration of the connection unit may ensure easy movement of the input/output unit.

Although the embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic diagnostic apparatus comprising:
    a main body;
    at least one input/output unit coupled to one side of the main body to input data to the main body or to output data transmitted from the main body; and
    a connection unit to connect the input/output unit and the main body to each other,
    wherein the connection unit includes:
        at least one first connection member connected at one end thereof to the main body and at the other end thereof to at least a portion of the input/output unit, wherein the at least one first connection member itself has a variable length to move the input/output unit relative to the main body; and
        a plurality of second connection members coupled to the first connection member and at least one of the main body or the input/output unit so as to come into contact with the same at a point to support load of the input/output unit,
    wherein the connection unit has a 3-dimensional arrangement in a plurality of planes.

2. The apparatus according to claim 1, wherein the at least one first connection member each includes a first main body coupling part coupled to the main body and a first input/output unit coupling part coupled to the input/output unit,
    wherein each of the second connection members includes a second main body coupling part coupled to the main body and a second input/output unit coupling part coupled to the input/output unit,
    wherein the first main body coupling part and the second main body coupling part are arranged in a first plane, and
    wherein the first input/output coupling part and the second input/output coupling part are arranged in a second plane.

3. The apparatus according to claim 2, wherein the first plane and the second plane are different planes.

4. The apparatus according to claim 3, wherein two second connection members and one first connection member are arranged to provide the connection unit with a triangular pyramid shape.

5. The apparatus according to claim 3, wherein two first connection members and two second connection members are arranged to provide the connection unit with a quadrangular pyramid shape.

6. The apparatus according to claim 3, wherein the first plane is at least one of a circular plane or an oval plane.

7. The apparatus according to claim 2, wherein the first main body coupling part, the first input/output unit coupling part, the second main body coupling part, and the second input/output coupling part are at least one of ball joints and universal joints.

8. The apparatus according to claim 1, wherein the connection unit is manually movable.

9. The apparatus according to claim 1, wherein the connection unit is automatically movable.

10. The apparatus according to claim 1, wherein the at least one input unit includes a control panel to input a signal to the main body.

11. The apparatus according to claim 1, wherein the at least one input unit includes a display to output a signal generated in the main body.

12. The apparatus according to claim 1, wherein at least one of the main body or the input/output unit is connected to the at least one first connection member and to at least one of the plurality of second connection members at a common point.

13. An ultrasonic diagnostic apparatus comprising:
    a main body;
    at least one input/output unit coupled to one side of the main body to input data to the main body or to output data transmitted from the main body; and
    a connection unit to connect the input/output unit and the main body to each other, the length of at least a portion of the connection unit itself being variable to allow the connection unit to move relative to the main body, wherein the connection unit is coupled at a plurality of points to at least one of the main body or the input/output unit to enable load distribution, wherein the connection unit has a 3-dimensional arrangement in a plurality of planes, and wherein the connection unit includes at least one first connection member itself having a variable length, and a plurality of second connection members coupled to the first connection member and at least one of the main body or the input/output unit.

14. The apparatus according to claim 13, wherein the at least one first connection member each includes a first main body coupling part coupled to the main body and a first input/output unit coupling part coupled to the input/output unit, wherein each of the second connection members includes a second main body coupling part coupled to the main body and a second input/output unit coupling part coupled to the input/output unit, and wherein the first input/output coupling part and the second input/output coupling part come into contact with each other at a point.

15. The apparatus according to claim 14, wherein the first main body coupling part and the second main body coupling part are arranged in a first plane, and the first input/output coupling part and the second input/output coupling part are arranged in a second plane, and wherein the first plane and the second plane are different planes.

16. The apparatus according to claim 15, wherein two second connection members and one first connection member are arranged to provide the connection unit with a triangular pyramid shape.

17. The apparatus according to claim 15, wherein two first connection members and two second connection members are arranged to provide the connection unit with a quadrangular pyramid shape.

18. The apparatus according to claim 15, wherein the first plane is at least one of a circular plane or an oval plane.

19. The apparatus according to claim 13, wherein the at least one first connection member and the plurality of second connection members correspond to the plurality of points, respectively, each of the first and second connection members extends from the corresponding point of the plurality of points to a common point on the other of the main body or the input/output unit.

* * * * *